United States Patent
Wang

Patent Number: 6,119,035
Date of Patent: Sep. 12, 2000

[54] METHOD AND SYSTEM FOR SYNTHESIZING THE 12-LEAD ELECTROCARDIOGRAM

[75] Inventor: Jyh-Yun J. Wang, Newton, Mass.

[73] Assignee: Hewlett-Packard Company, Palo Alto, Calif.

[21] Appl. No.: 09/048,632

[22] Filed: Mar. 26, 1998

[51] Int. Cl.[7] .................................................. A61B 5/0428
[52] U.S. Cl. ............................................................. 600/509
[58] Field of Search ................................... 600/509, 512, 600/521

[56] References Cited

U.S. PATENT DOCUMENTS

| | | | |
|---|---|---|---|
| 4,850,370 | 7/1989 | Dower | 600/509 |
| 5,058,598 | 10/1991 | Nicklas et al. | 600/509 |
| 5,318,037 | 6/1994 | Evans et al. | 600/509 |
| 5,377,687 | 1/1995 | Evans et al. | 600/609 |
| 5,711,304 | 1/1998 | Dower | 600/509 |

OTHER PUBLICATIONS

Schere et al., Synthesis of the 12–lead electrocardiogram from a 3–lead semi–orthogonal subset using patient specific linear transformation matrix, Computers in Cardiology 1988, IEEE Comput. Soc. Press, 1989. Abstract.

*Primary Examiner*—Jeffrey R. Jastrzab

[57] ABSTRACT

A method and system are provided for quickly and efficiently producing multiple syntheses of 12-lead electrocardiographs utilizing fewer than the 12 leads provided by a full electrode set. The method and system achieve their objects as follows. One or more 12-lead electrocardiograph leads are synthesized from a first subset of a patient's physically present 12-lead electrocardiograph leads. In response to user-defined parameters, one or more 12-lead electrocardiograph leads are synthesized from a second subset, different than the first subset, of a patient's physically present 12-lead electrocardiograph leads. Also set forth are a method and system are provided for synthesizing a 12-lead electrocardiograph utilizing fewer than the 12 leads provided by a full electrode set. Therein, a subset of the full electrode set is attached to a patient. A subset of 12-lead electrocardiograph leads formed by the attached subset is identified. In response to the identified subset of 12-lead electrocardiograph leads, a synthesis matrix is recalled. In response to the recalled synthesis matrix, an accuracy factor associated with the recalled synthesis matrix is recalled. And, one or more 12-lead electrocardiograph leads are synthesized by applying the recalled synthesis matrix and the recalled accuracy factor to the identified subset of 12-lead electrocardiograph leads formed by the attached subset. Also set forth are a method and system for assessing the accuracy of synthesis electrocardiograph leads. Therein, one or more additional electrodes are attached to the patient. One or more 12-lead electrocardiograph leads are generated from the attached one or more additional electrodes. And, the generated one or more 12-lead electrocardiograph leads are compared with correspondent synthesized one or more 12-lead electrocardiograph leads.

50 Claims, 5 Drawing Sheets

METHOD AND SYSTEM FOR SYNTHESIZING THE 12-LEAD ELECTROCARDIOGRAM

BACKGROUND

1. Technical Field

The present invention relates, in general, to a method and system for providing waveform representations of heart function, such as those produced by the electrocardiograph. In particular, the present invention relates to a method and system for providing waveform representations of heart function, such as those produced by the electrocardiograph, by synthesizing a standard 12-lead electrocardiograph from a subset of electrodes utilized to derive the standard 12-lead electrocardiograph.

2. Description of Related Art

The present invention presents a method and system for synthesizing a standard 12-lead electrocardiograph from a subset of electrodes utilized to derive the standard 12-lead electrocardiograph. In order to understand why such synthesis is useful, it is helpful to have a basic understanding of the "gold standard" 12-lead electrocardiograph. Accordingly, as an aid to understanding the electrocardiograph, the discussion below presents a brief description of (1) the electrochemical and mechanical operation of the heart, (2) how the electrochemical operation of the heart is transduced into electrical energy which is then used by the electrocardiograph to graphically denote the mechanical operation of the heart, and (3) how the certain specific electrical signals (or "leads") are derived from the electrocardiograph.

The mechanical events of the heart are preceded and initiated by the electrochemical activity of the heart (i.e., the propagation of the action potential). There is a device which transforms the electrochemical activity of the heart into a form visible to the human eye: the electrocardiograph, which produces a visual representation of the electrochemical activity of the heart. The visual representation is known as the electrocardiogram (EKG).

During an EKG, electrodes are attached to the body surface. The electrodes are specially treated to allow the charge carriers within the electrodes (electrons) to communicate with the charge carriers within the body (ions) via electrochemical exchange. Attaching electrodes to the body surface allows the voltage changes within the body to be recorded after adequate amplification of the signal. A galvanometer within the EKG machine is used as a recording device. Galvanometers record potential differences between two electrodes. The EKG is merely the recording of differences in voltage between two electrodes on the body surface as a function of time, and is usually recorded on a strip chart. When the heart is at rest, diastole, the cardiac cells are polarized and no charge movement is taking place. Consequently, the galvanometers of the EKG do not record any deflection. However, when the heart begins to propagate an action potential, the galvanometer will deflect since an electrode underneath which depolarization has occurred will record a potential difference from a region on the body under which the heart has not yet depolarized.

A complete heart cycle is known as a heartbeat. On an EKG, a normal heartbeat has a distinctive signal. Initially, the galvanometer notes a relatively short duration rounded positive deflection (known as the P wave), which is caused by atrial depolarization. Subsequent to this, there is a small but sharp negative deflection (known as the Q wave). Next, there is a very large and sharp positive deflection (known as the R wave), after which there is a sharp and large negative deflection (known as the S wave). When these waves are taken together, they are known as the QRS complex. The QRS complex is caused by ventricular depolarization. Subsequent to the QRS complex, is a relatively long duration rounded positive deflection (known as the T wave), which is caused by ventricular repolarization.

The EKG, in practice, uses many sets of electrodes. But these electrodes are so arranged on the surface of the body such that the signals received will have the similar shape as that just described. Well-known bipolar pairs of electrodes are typically located on a patient's right arm (RA), left arm (LA), right leg (RL) (commonly used as a reference), and left leg (LL). Unipolar electrodes referenced properly are referred to as V leads and are positioned anatomically on a patient's chest according to an established convention (labeled as follows as Leads V1–V6). In heart monitoring and diagnosis, the voltage differential appearing between two such electrodes or between one electrode and the average of a group of other electrodes represents a particular perspective of the heart's electrical activity and is generally referred to as the EKG. Particular combinations of electrodes are called leads. For example, the leads which may be employed in a "gold standard" 12-lead electrocardiogram system are:

Lead I=(LA−RA)
Lead II=(LL−RA)
Lead IIII=(LL−LA)
Lead aVR=RA−(LA+LL)/2
Lead aVL=LA−(RA+LL)/2
Lead aVF=LL−(LA+RA)/2
Lead V1=V1−(LA+RA+LL)/3
Lead V2=V2−(LA+RA+LL)/3
Lead V3=V3−(LA+RA+LL)/3
Lead V4=V4−(LA+RA+LL)/3
Lead V5=V5−(LA+RA+LL)/3
Lead V6=V6−(LA+RA+LL)/3

Thus, although the term "lead" would appear to indicate a physical wire, in electrocardiography the term actually means the electrical signal taken from a certain electrode arrangement as illustrated above.

Furthermore, it will be understood by those within the art that there are certain instances (e.g., when monitoring neonate patients or patients with right-side infarct) where some electrocardiographic electrodes are placed on the right side of the chest. For example, it is well known within the art that right side variations of 12-lead electrocardiographic leads V3, V4, and V5 exist and are referred to within the art as V3R, V4R, and V5R. It is to be understood that well-known variations, such as the examples cited, are to fall within the rubric of the 12-lead electrocardiograph and its attendant electrode placements (and subsets of the 12-lead electrocardiograph and its attendant electrode placements) as such is used herein.

Over the years, health care professionals have built up a body of knowledge wherein they have learned to correlate variations in the EKG with different diseases and heart defects. Formally, this process of correlating is known as "electrocardiography."

Electrocardiography, as practiced by human cardiologists, is primarily a visually oriented art in that the human cardiologists visually inspects a waveform tracing of electrocardiographic measurements taken over time, and on the basis of the morphological (i.e., shape) changes of the waveform over time the human cardiologist makes a diagnosis of heart function. In making such diagnosis, it is essential that the human cardiologist have an accurate characterization of waveform representation, derived from the electrocardiographic measurements, of heart function in that inaccuracies in the waveform will give rise to inaccuracies in diagnosis.

The requirement for an accurate characterization of waveform representation is even more critical for mechanized electrocardiography. That is, machines have been created which have automated many of the functions traditionally performed by human cardiologists.

As has been alluded to, the "gold standard" for accurate characterization of waveform representation of heart function is the 12-lead electrocardiograph described above. Indeed, many of the diagnoses and techniques, which have been developed over the years, are dependent upon the presence of all 12 leads of the "gold standard" electrocardiograph.

However, as is apparent from the above discussion, the "gold standard" 12-lead electrocardiograph requires the accurate preparation and placement of 10 electrodes to derive the 12 leads. Furthermore, each electrode has associated with it a wire which connects the electrode to the electrocardiograph proper. Consequently, obtaining the "gold standard" electrocardiograph requires considerable time and precision associated with accurately preparing and placing the 10 electrodes; furthermore, even after the electrodes are correctly prepared and placed, significant clutter exists arising from the wires and connectors associated with each electrode.

The foregoing problems associated with electrode preparation, placement, and wire clutter have been recognized. Consequently, attempts have been made to "synthesize" the "gold standard" 12-lead electrocardiograph utilizing less than the 10 electrodes ordinarily required to produce the 12-lead electrocardiograph.

Three of the better known attempts to synthesize the 12-lead electrocardiograph have been to synthesize the 12-lead electrocardiograph utilizing the EASI lead system, to synthesize the 12-lead electrocardiogram utilizing the Frank vectorcardiograph lead system, and to synthesize the 12-lead electrocardiogram utilizing a patient-specific 12-lead transformation (invented by Julie Scherer and John Nicklas). Each of these systems will now be discussed in turn.

In the EASI lead system, an attempt is made to derive the full 12-lead EKG from a non-standard 5-electrode lead placement (denoted as the EASI lead system). The 12-lead electrocardiogram is derived from non-standard 5-electrode lead placement via the use of a patient-independent transformation for deriving the 12-lead EKG from the EASI leads. This patient independent transformation was produced via the cross-correlation of twenty-seven simultaneously acquired 12-lead EKGs and EASI EKGs. G. E. Dower, *Method and Apparatus for Sensing and Analyzing Electrical Activity in the Human Heart*, U.S. Pat. No. 4,850,370 (1989) (hereby incorporated in its entirety). The reason the non-standard 5-electrode lead placement was used was because Dower was trying to devise the best electrode placement which would yield essentially linearly independent signals from which the 12-lead EKG could be derived. As has been emphasized by the foregoing italicization and underlining, all 12 leads provided by the EASI lead system, including all the limb leads, are derived, which means that none of the leads corresponding to any of the leads in the "gold standard" 12-lead electrocardiogram can be acquired directly by use of the EASI system. Furthermore, it is to be understood that because the EASI synthesis requires the presence of all leads formed by the EASI electrodes attached to a patient, the loss of even one electrode will disable the EASI synthesis process.

Given the fact that all leads in the EASI system are derived, the question naturally arises as to how accurate such derived leads are, when compared with actual 12-lead electrocardiograph simultaneously obtained from the same patient. At present, the only known method for making such assessment is the simultaneous application of the EASI 5 electrode set, and the 12-lead EKG 10 electrode set, to the same patient.

In the Frank system, instead of viewing the activity of the heart as a potential difference plotted against a time base as in the electrocardiogram, the activity of heart is viewed as a "spinning" or "rotating" "vector" of varying magnitude located within the three dimensional space of the chest cavity. In the Frank system, the idea is that the "tip" of the vector is intended to be indicative of the motion of that action potential as it spreads throughout the heart. Thus, the idea is that a cardiologist can get a feel for what is occurring within the heart by watching how the action potential is flowing through the heart as is indicated by the Frank "vector." G. E. Dower, *Method and Apparatus for Sensing and Analyzing Electrical Activity in the Human Heart*, Columns 2–3, U.S. Pat. No. 4,850,370 (1989) (discussing the Frank vectorcardiograph).

The leads constructed from the electrode set utilized to produce the Frank "vectorcardiograph" are nearly orthogonal. Consequently, they produce nearly linearly independent leads, or signals, and thus (as was discussed above in relation to the EASI leads) the Frank leads are interpreted to form good candidates for synthesis of the 12-lead electrocardiograph. However, since the Frank system electrode placement is again different from the 12-lead electrocardiograph lead placement, there is no way to track the accuracy of the synthesis derived from the Frank system except to simultaneously attach and run a 12-lead electrocardiograph in the fashion as was described in relation to testing the accuracy of the EASI system. Furthermore, it is to be understood that because the Frank synthesis requires the presence of all leads formed by the Frank electrodes attached to a patient, the loss of even one electrode will disable the synthesis process.

In the patient-specific 12-lead transformation, a patient-specific 5-electrode system (using a standard 5-electrode lead system, seven leads can be obtained, including all six limb leads (I, II, III, aVR, aVL, and aVF) and a chest lead (V)) is utilized to synthesize a 12-lead electrocardiogram. As the name of the attempt indicates, the synthesis is achieved via the use of a patient-specific transformation. J. Nicklas and J. Scherer, *Method And Apparatus for Synthesizing Leads of An Electrocardiogram*, U.S. Pat. No. 5,058,598 (Oct. 22, 1991). The patient-specific transformation is achieved as follows. For each patient a conventional full 12-lead EKGs is first taken. From this 12-lead data, a patient-specific transformation which can be used to synthesize a 12-lead EKG from 3 semi-orthogonal leads (such as I, II, and V2) is identified or created via the use of near-real-time numerically and computationally intensive data processing.

It has been found that the baseline performance of this patient-specific transformation can be further improved by segmenting the synthesized EKG waveforms into PR, QRS and ST segments. It has been shown that by adaptively segmenting the EKG, typically 12 to 24 segments, the error rate on reconstruction can be further reduced. However, this segmentation to achieve the gain in accuracy has resulted in a significant increase in processing requirements in obtaining the patient-specific transformation.

There are significant shortcomings with respect to the foregoing described attempts to synthesize the 12-lead EKG from a less than 10 electrode set, a few of which will be detailed here. Both EASI and Frank lead syntheses have at least three significant shortcomings, present in all of their incarnations: (1) both the EASI and Frank systems utilize a fixed, non-standard, lead system, which requires technicians to learn and be familiar with lead systems beyond those normally associated with the 12-lead EKG and its standard subsets (which is definitely a potential source of human error, since accuracy of lead placement has been shown to be difficult for a large percentage of nurses, Drew, Ida and Sparacino, *Accuracy of Bedside Electrocardiographic Monitoring: A report on Current Practices of Critical Care Nurses*, Heart & Lung 1991; Vol. 20, No 6, 597–609); (2) because in both the EASI and Frank syntheses all leads are derived there is no easy way to check the accuracy of the derived leads; and (3) both the EASI and Frank syntheses require the presence of all their leads to effect synthesis. With respect to lead placement, as can be seen by the description of the 12-lead system, above, the number and positioning of electrode placements makes the complexity of the 12-lead system high, making it difficult to learn; thus, the EASI and Frank requirements of learning new lead systems and electrode placements add more complexity and a likelihood of an increase in human error. With respect to accessing the accuracy of the derived leads, it was discussed above that the only way to check either the EASI or Frank 12-lead syntheses is to actually connect a separate 12-lead system simultaneous with the EASI or Frank systems to check for accuracy. And, with respect to the fact that both the EASI and Frank syntheses require the presence of all leads, the EASI and Frank systems are not robust in that the loss of even one EASI or Frank electrode will disable both the EASI on Frank syntheses.

The patient-specific transformation system, in all its different incarnations, has at least five significant shortcomings that will be appreciated by those within the art: (1) the system requires the presence, and previous use of, a 12-lead electrocardiograph in order to gather data from which a patient-specific transformation can be produced; (2) the system, even in its most basic and stripped-down incarnation, is computationally and numerically intensive, with such computational and numerical intensiveness increasing as more accurate versions of the system are implemented; (3) the system requires that a base set of leads be chosen and then that a transformation be calculated for such chosen base set, and consequently requires the recalculation of a patient-specific transformation every time clinical requirements force the selection of a new base set; (4) the accuracy of the patient-specific transformation is directly proportional to the duration of which the standard 12-lead electrocardiograph is attached to the patient; and (5) no mention is made as to how the accuracy of leads synthesized can be verified or checked.

Thus, EASI and Frank syntheses require the use of fixed lead sets utilizing electrode placement not compatible with the standard 12-lead electrocardiograph, while the patient-specific transformation requires that a 12-lead electrocardiograph be measured and then utilized to compute a transformation for a particular lead set for a particular patient. The foregoing gives rise to a number of difficulties.

With respect to EASI and Frank systems, the non-standard lead sets increase the amount of training necessary for personal and make it difficult to check the EASI/Frank syntheses for accuracy. With respect to the patient-specific transformation, the requirement that a 12-lead electrocardiograph be taken increases the time and effort necessary to eventually construct the synthesis; furthermore, in many cases, such obtainment of the 12-lead EKG baseline data is not practicable, such as cases where a patient has a surgical wound at the location where one would need to apply the electrode.

There have been attempts in the past to synthesize one or more leads of a 12-lead electrocardiograph using fewer than the standard number of ten electrodes. However, these systems have all produced unacceptable results. Nicklas at column 2, lines 35–54.

With respect to the foregoing, it is apparent that a need exists for a method and system which will allow the following: (1) synthesis, by use of patient-independent transformations, of one or more leads of the 12-lead electrocardiograph from one or more subsets of the 12-lead electrocardiograph electrode placements and wherein such synthesis produces user acceptable results; (2) a way of showing the accuracy of the synthesis as a whole and/or synthesis leads based on the particular subset of the 12-lead electrocardiograph electrodes in use; (3) a quick and easy real-time check on the accuracy of the one or more synthesized leads; (4) the quick and easy addition or removal of 12-lead electrocardiographic electrodes from the initial subset used, and subsequent synthesis, by use of a transformation, of one or more leads of the 12-lead electrocardiograph on the basis of the resulting subset of electrodes and leads derived therefrom; and (5) optionally, provide all foregoing described synthesis operations but with the use transformations which, although still patient-independent, are geared to a particular patient-profile.

SUMMARY OF THE INVENTION

It is therefore one object of the present invention to provide a method and system for providing waveform representations of heart function, such as those produced by the electrocardiograph.

It is another object of the present invention to provide a method and system for providing waveform representations of heart function, such as those produced by the electrocardiograph, by synthesizing a standard 12-lead electrocardiograph from a subset of electrodes utilized to derive a standard 12-lead electrocardiograph.

A method and system are provided for quickly and efficiently producing multiple syntheses of 12-lead electrocardiographs utilizing fewer than the 12 leads provided by a full electrode set. The method and system achieve their objects as follows. One or more 12-lead electrocardiograph leads are synthesized from a first subset of a patient's physically present 12-lead electrocardiograph leads. In response to user-defined parameters, one or more 12-lead electrocardiograph leads are synthesized from a second subset, different than the first subset, of a patient's physically present 12-lead electrocardiograph leads. Also set forth are a method and system are provided for synthesizing a 12-lead electrocardiograph utilizing fewer than the 12 leads provided by a full electrode set. Therein, a subset of the full electrode set is attached to a patient. A subset of 12-lead electrocardiograph leads formed by the attached subset is identified. In response to the identified subset of 12-lead electrocardiograph leads, a synthesis matrix is recalled. In response to the recalled synthesis matrix, an accuracy factor associated with the recalled synthesis matrix is recalled. And, one or more 12-lead electrocardiograph leads are synthesized by applying the recalled synthesis matrix and the recalled accuracy factor to the identified subset of 12-lead electrocardiograph leads formed by the attached subset. Also set forth are a method and system for assessing the accuracy of synthesis electrocardiograph leads. Therein, one or more additional electrodes are attached to the patient. One or more 12-lead electrocardiograph leads are generated from the attached one or more additional electrodes. And, the generated one or more 12-lead electrocardiograph leads are compared with correspondent synthesized one or more 12-lead electrocardiograph leads.

The method and system provide the advantages of providing a number of different patient-independent "synthesis matrices" for a number of different electrode sets, thereby allowing the application of various electrode sets to a patient, and the synthesis of one or more leads of the 12-lead electrocardiograph from such changing electrode sets, on almost a real-time basis. Thus, the method and system allow nearly continuous synthesis of the 12-lead electrocardiograph, even though the electrode set in use may be changing as a patient's clinical requirements change. In addition, since the method and system provide synthesis by utilizing a subset of the standard 12-lead electrode set, any synthesized lead can be checked by merely adding one or more other electrodes, and if the synthesized lead is found to be inaccurate the newly added one or more electrodes can be utilized in its stead and synthesis can then be obtained via use of the new lead set actually present.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF PREFERRED EMBODIMENT

Figure 1:
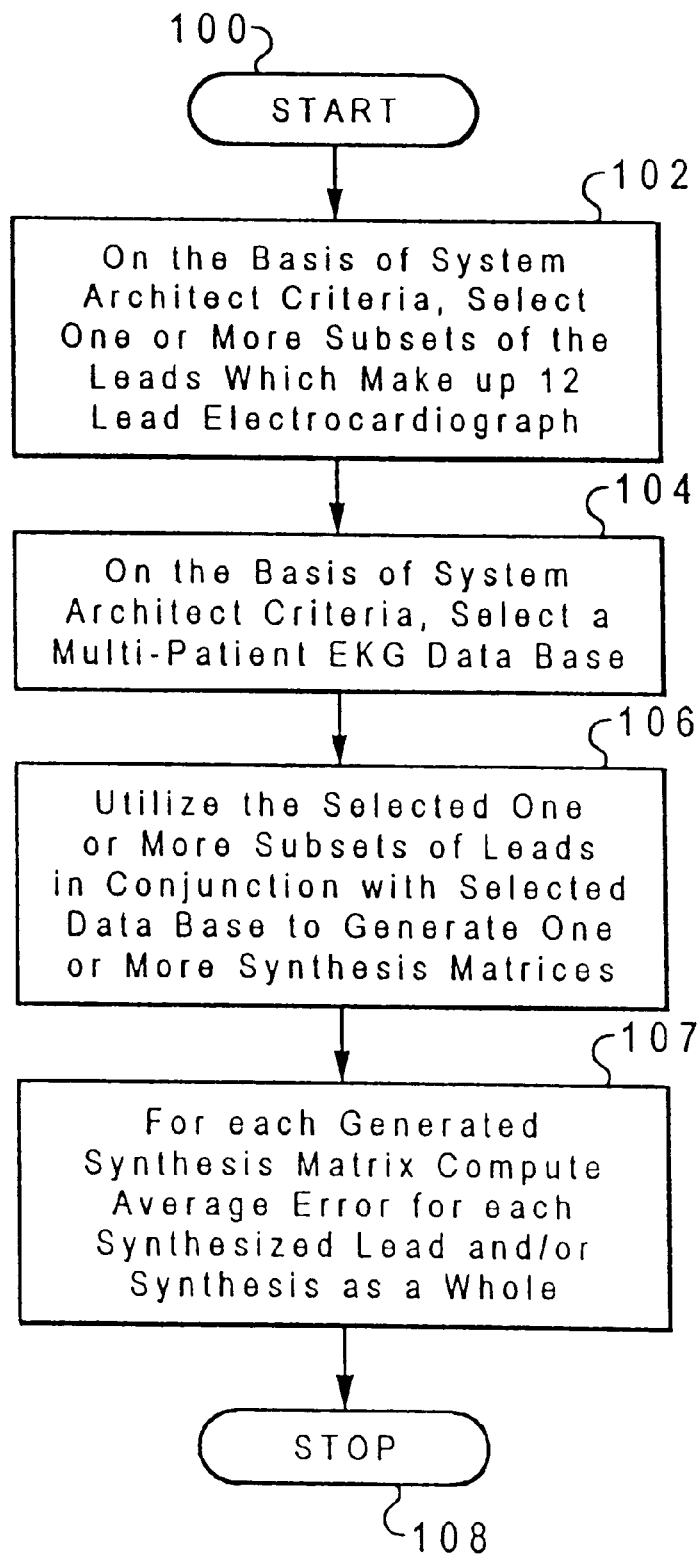
FIG. 1 is a high-level logic flowchart which depicts a method by which an illustrative embodiment of the present invention generates patient-independent "synthesis matrices"

The following description describes a method and system which utilizes electrocardiographic measurements. The method and system are related to the provision of highly accurate characterizations of waveform representations of heart function, such as QRS complexes, where such waveform representations are constructed from electrocardiographic measurements.

An illustrative embodiment of the present invention is composed of a method and system which can produce a synthesis of a 12-lead electrocardiogram via the use of a user-selectable subset of leads arising from a subset of the electrodes normally utilized to construct the 12-lead electrocardiogram. This embodiment presents at least two advantages not previously available: (1) it allows the synthesis of the 12-lead electrocardiogram from a patient utilizing whatever leads practicable to obtain, given the physical limitations of the patient (e.g. what areas of a patient's body are easily accessible for electrode placement) and; (2) since the synthesis utilizes the standard 12-lead electrocardiogram electrode configuration, such synthesis can be checked merely by adding an additional 12-lead electrocardiogram electrode and comparing the resulting actual lead with the synthesized lead.

The illustrative embodiment achieves the foregoing by the empirical production of patient-independent "synthesis matrices" for every likely possible electrode lead combination, and then utilizing the appropriate patient-independent "synthesis matrix" dependent upon the number of electrodes attached to the patient, and (optionally) such patient-independent "synthesis matrices" can also be further based on specific profiles (e.g., heart damage location, age of patient, gender, weight, etc.) of patient populations with which such synthesis is to be used.

The first step in producing an illustrative embodiment is to determine and list all possible combinations of two or more of the leads extant in the 12-lead electrocardiograph for which synthesis might be desirable.

It will be recognized by those within the art that the fact that there are 12 leads available gives rise to a relatively large number of mathematically possible lead combinations (e.g., there are 132 possible two lead combinations, 1320 three-lead combinations, 11880 four-lead combinations, etc.); however, it will also be understood by those within the art that, while many combinations are mathematically possible, there is a significantly smaller number of such combinations that are likely to yield more accurate syntheses of the 12-lead electrocardiograph (e.g., leads arising from electrodes positioned such that the lead signals are more nearly "orthogonal" or linearly independent). In addition, the actual electrodes present in any particular situation will in themselves limit the number of combinations that are actually of interest to a clinician. For example, in the case where all limb lead electrodes (RA, LA, LL) and 2 chest electrodes are available, only 4 additional chest leads need to be derived. Thus, since there are only six chest electrode positions which may be filled by the two chest electrodes, the number of possible electrode combinations is limited to 15.

It will also be recognized that many times physiological constraints will make certain combinations of leads more desirable than others (e.g., a situation where synthesis is likely to occur with a patient who has surgical wounds making one or more of the standard electrode placements impractical, or a situation wherein heart damage is localized such that one or more specific leads are critical). It has also been found that a good 12-lead electrocardiograph can be synthesized by using a 6-electrode lead set giving rise to at least two chest leads, such that one of the two chest leads is placed at either the V1 or V2 position, and such that the other of the two chest leads is placed at either the V5 or V6 position.

Once such combinations have been selected, the next step is to select a data base consisting of many EKGs from a number of patients. This data base selection can, but not necessarily must, be selected to match a patient profile of the type of patients with which the resultant patient-independent synthesis matrix is to be used. That is, it will be understood by those within the art that the foregoing described technique could be utilized to produce various and different sets of patient-independent synthesis matrices which are paired with various and different specific profiles of patient populations likely to be monitored. For example, one set of patient-independent synthesis matrices could be produced to be utilized with persons with relatively normal heart function by use of EKG data collected from patients in a population of relatively normal hearts, while other sets of patient-independent synthesis matrices could be produced to be utilized with persons with specific types of heart damage or other physiological characteristics.

Thereafter, for each lead combination for which synthesis is desired, the desired lead combination and selected data base are utilized in conjunction with any of a number of well-known numerical processing techniques to derive a linear transformation by which the selected lead combination can be "transformed" (i.e., synthesized) into a 12-lead electrocardiogram. Typically (although not always), such techniques yield at least one matrix for each desired lead combination which can be multiplied times the lead combination, in column vector format, to produce a 12×1 column vector where each row entry equates to one of the 12 leads of the 12-lead EKG. The two prior art references (Dower, Nicklas) cited earlier and incorporated by reference provide at least two of such well known techniques for creating such a linear transformation. Furthermore, it will be recognized by those within the art that many such techniques can be found in virtually any graduate level numerical methods textbook.

Once the desired patient-independent synthesis matrices have been obtained, they can be thereafter utilized, as appropriate, with one or more subsets of the leads composing the 12-lead electrocardiograph in order to produce a synthesis of the 12-lead electrocardiograph.

Refer now to FIG. 1. FIG. 1 is a high-level logic flowchart which depicts a method by which an illustrative embodiment of the present invention generates patient-independent synthesis matrices. Method step 100 shows the start of the process. Method step 102 depicts the selection, based upon system architect criteria (which, as has been discussed, could be composed of any number of factors, such as the linear independence of the leads, or the anatomical localization of heart damage), of one or more subsets of the leads which make up the 12-lead electrocardiograph.

Thereafter, method step 104 illustrates the selection of a multi-patient EKG data base, wherein such selection is based upon system architect criteria (which, as discussed, could be composed of any number of factors, such as the projected patient population profile with which the one or more resultant patient-independent synthesis matrices are to be used).

Method step 106 shows the utilization of standard numerical/mathematical processing techniques in conjunction with both the selected one or more subsets of the leads which compose the 12-lead EKG and the selected multi-patient EKG data base to produce one or more patient-independent synthesis matrices.

Method step 107 depicts the utilization of standard numerical/mathematical processing techniques in conjunction with the selected one or more subsets of the leads which compose the 12-lead EKG, the selected multi-patient databases, and the produced one or more patient independent synthesis matrices to produce an "accuracy factor" (or, "average error") indication for each lead to be synthesized. Such error being, for example, the standard deviation of the synthesized leads from the averaged actual leads taken from the selected multi patient data base. Additionally or alternatively, an average error could be produced for each synthesis matrix indicating the overall error of the synthesis leads associated with such synthesis matrix.

Method step 108 depicts the end of the process.

Figure 2A:
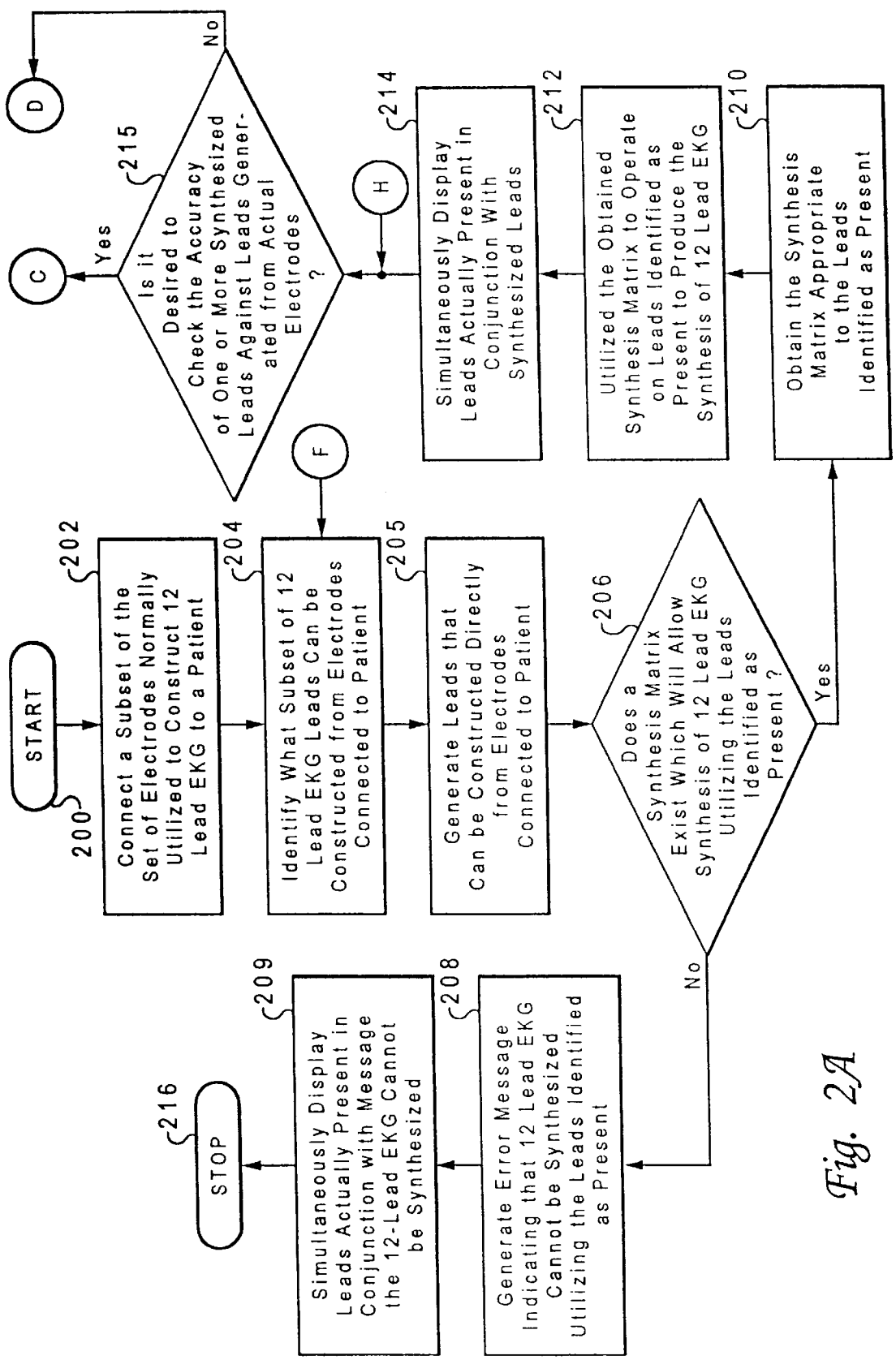
FIGS. 2A, 2B and 2C together constitute a high-level logic flowchart which depicts a method by which an illustrative embodiment of the present invention utilized patient-independent "synthesis matrices" to generate a synthesis of the 12-lead EKG from a subset of the 12-lead EKG.
Figure 2B:
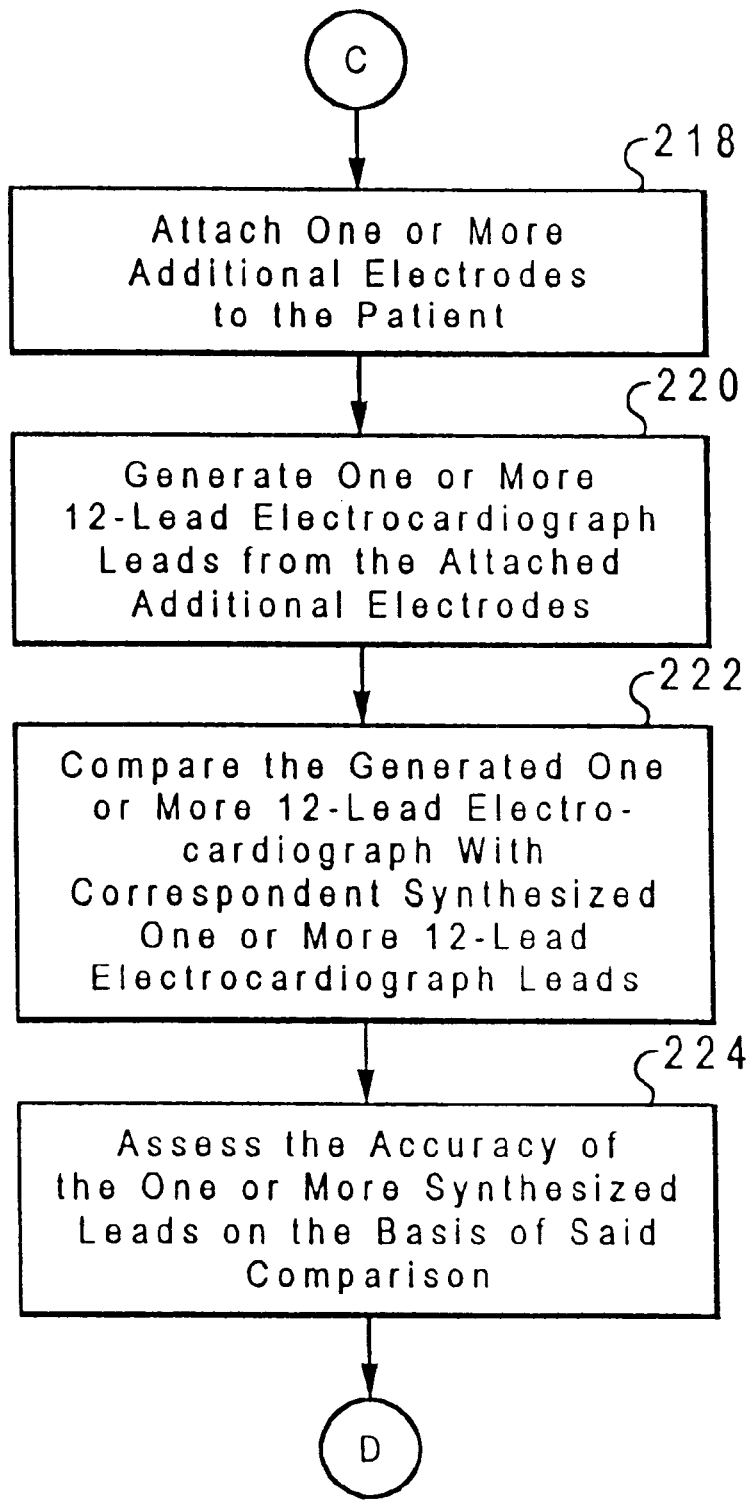
Figure 2C:
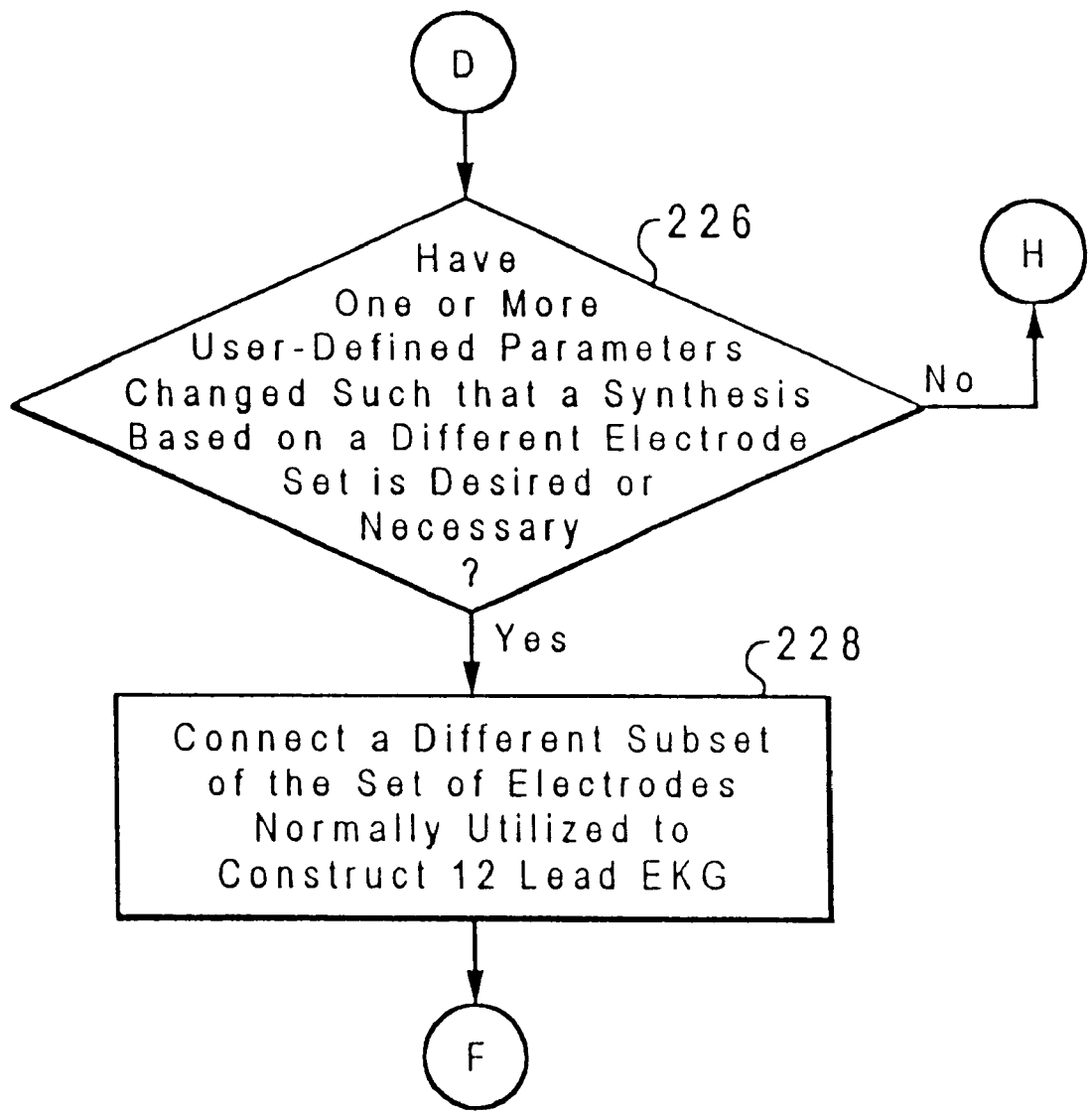

Refer now to FIGS. 2A, 2B, and 2C. FIGS. 2A, 2B, and 2C together constitute a high-level logic flowchart which depicts a method by which an illustrative embodiment of the present invention utilizes patient-independent synthesis matrices to generate a synthesis of the 12-lead EKG from a subset of the 12-lead EKG. Method step 200 shows the start of the process. Method step 202 shows the connection of a subset of the set of electrodes normally utilized to construct the 12-lead EKG to a patient.

Thereafter, method step 204 depicts the identification of what subset of the 12-lead EKG leads are formed, or can be constructed directly from, the electrodes connected to the patient; it will be understood by those within the art that such identification could be done manually by an EKG machine technician, or could be done automatically by machine. Method step 205 illustrates the generation of the leads identified; such generated leads will ultimately be displayed as non-synthesized leads.

In response the identification of what particular subset of the standard 12-lead set is formed by the electrodes connected to the patient, method step 206 illustrates the determination of whether a patient-independent synthesis matrix exists which will allow the synthesis of the 12-lead EKG from the leads present. In the event that such an appropriate patient-independent synthesis matrix is not present, method step 208 shows that an error message is generated which indicates that a 12-lead EKG cannot be synthesized from the leads identified as present. Subsequently, the process proceeds to method step 209 which depicts the display of the generated error message indicating that leads cannot be synthesized in conjunction with the leads actually present, which were generated in method step 205. Thereafter, the process proceeds to method step 216 and stops. However, in the event that a patient-independent synthesis matrix appropriate to the subset of leads identified is present, the process proceeds to method step 210.

Method step 210 depicts that the patient-independent synthesis matrix appropriate to the leads identified as present is obtained (which, in one illustrative embodiment, amounts to recalling the patient-independent synthesis matrix from computer memory). Method step 212 illustrates that the obtained patient-independent synthesis matrix is then utilized to operate upon (which in one illustrative embodiment amounts to matrix multiplication) the subset of leads identified as present to produce the synthesis of the remaining leads of the 12-lead EKG which are not formed by, or cannot be constructed from, the subset of electrodes in use.

Thereafter, method step 214 shows the substantially simultaneous display and designation of both the leads which can be constructed from the subset of electrodes in use (i.e., those leads generated in method step 205) and the leads resulting from the application of the patient-independent synthesis matrix to those leads (i.e., the synthesized leads). Although not expressly shown, it is to be understood that method step 214 is also illustrative of any analysis or signal processing that may be performed upon any combination of actual or synthesized signal.

Thereafter method step 215 depicts the inquiry of whether it is desired to check the accuracy of one or more synthesized leads against leads generated from actual electrodes. If no such check is desired, the process proceeds to method step 228; however, if such check is desired, the process proceeds to method step 218. Method step 218 shows the attachment of one or more additional electrodes to the patient. Method step 220 depicts the generation of one or more 12-lead electrocardiograph leads from the attached additional electrodes. Method step 222 illustrates the comparison of the generated one or more generated 12-lead electrocardiograph lead with the synthesized one or more leads which are representative of the actual leads. Method step 224 shows that the accuracy of one or more synthesized leads is then assessed based upon the comparison illustrated in method step 222.

Thereafter, the process proceeds to method step 226 which depicts an inquiry of whether one or more user defined parameters have changed such that a synthesis based on a different electrode set is desired or necessary. (Examples of such user defined parameters could be user preference, changing patient acuity, or changing data processing requirements.) If no such change has occurred, then the process proceeds to method step 215. However, if such change has occurred, the process proceeds to method step 228. Method step 228 illustrates the connection of an electrode set different from the previously connected. Thereafter, the process proceeds to method step 204.

Furthermore, it will be understood by those within the art that the process illustrated by FIGS. 2A, 2B and 2C can be progressively re-engaged in when additional one or more electrodes are added or one or more existing electrodes are removed or repositioned. Such re-engagement in the process giving rise to a new synthesis based on the new electrode configuration and leads resulting from same.

Figure 3:
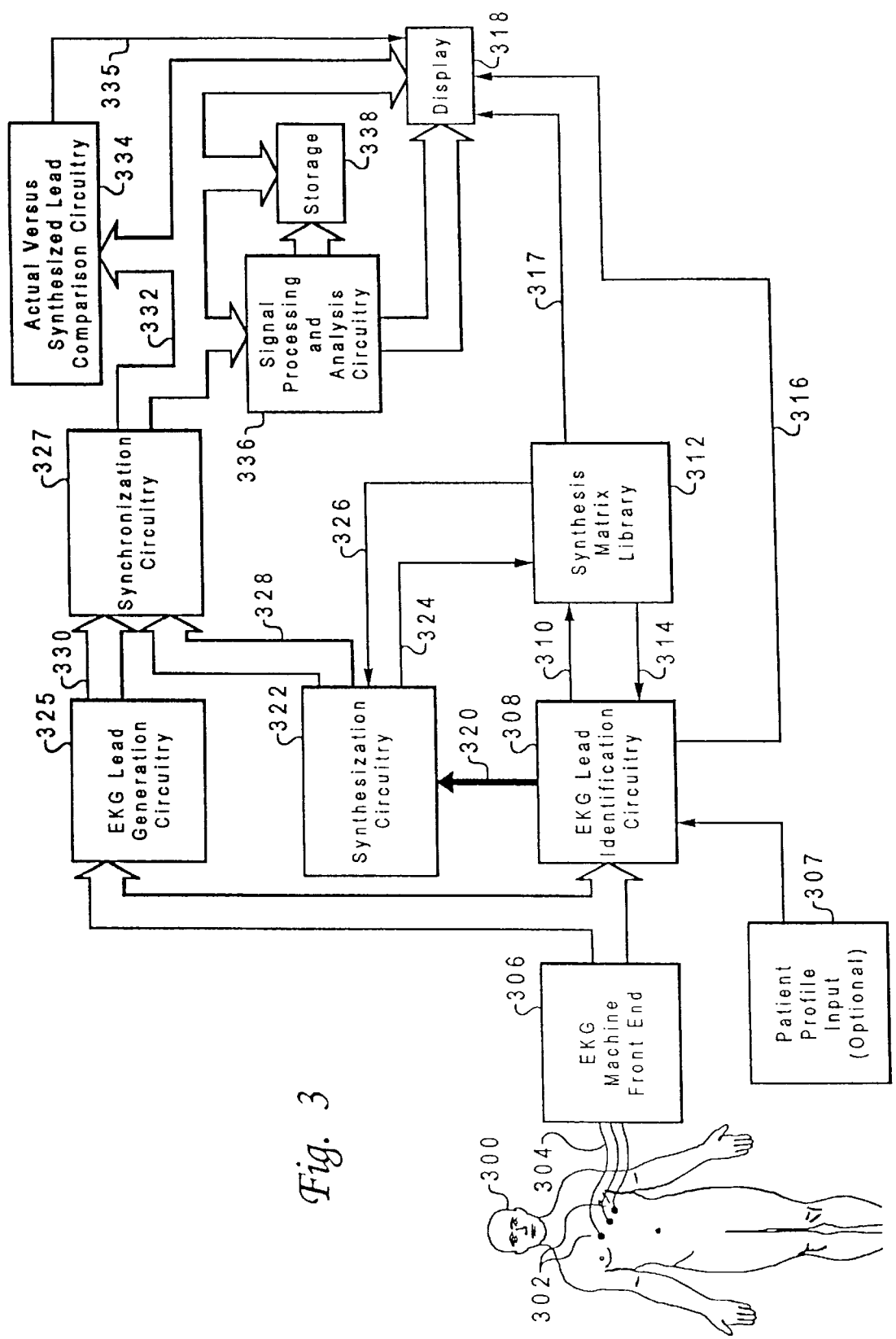
FIG. 3 illustrates one embodiment of a system that can be utilized in accord with the present invention.

Refer now to FIG. 3. FIG. 3 illustrates one embodiment of a system that can be utilized in accord with the present invention. Shown in FIG. 3 is a patient 300 to which have been affixed, or connected electrodes 302 which form a subset of those electrodes normally utilized to construct the 12-lead EKG. These electrodes are connected by electrode wires 304 to EKG machine front end 306. Thereafter, shown is that the electrical signals produced by the connected electrodes are routed to EKG lead identification circuitry 308, which identifies what leads are formed by the subset of the electrodes normally utilized to construct the standard 12-lead EKG. Furthermore, optional component patient profile input 307 illustrates that in one embodiment of the present invention, a technician (not shown) can designate a patient-profile into which patient 302 is likely to fall.

Upon identification of the leads present, EKG lead identification circuitry 308 sends a signal 310 to patient-independent synthesis matrix library 312, identifying what leads have been identified as present (and, optionally, what patient-profile has been designated). In response to this signal, patient-independent synthesis matrix library 312 returns a signal 314 indicating either that a patient-independent synthesis matrix exists which can synthesize the 12-lead EKG from the leads identified as present (and, optionally, what patient-profile has been designated) or that a patient-independent synthesis matrix is not available for the leads identified as present (and, optionally, what patient-profile has been designated). In response to the content of signal 314, EKG lead identification circuitry 308 either sends display error message signal 316 to display 318, or sends retrieve patient-independent synthesis matrix message 320 to synthesization circuitry 322.

In response to retrieve synthesization matrix message 320, synthesization circuitry 322 queries 324 patient-independent synthesis matrix library 312 for the patient-independent synthesis matrix appropriate to the leads (and, optionally, what patient-profile has been designated) identified by lead identification circuitry 308. In response to query 324, patient-independent synthesis matrix library 312 (1) retrieves the synthesization matrix appropriate to the leads identified (and, optionally, what patient-profile has been designated) from patient-independent synthesis matrix library 312 and sends the patient-independent synthesis matrix to synthesization circuitry 322 via query response 326, and (2) retrieves average error information (e.g. average error per individual synthesized lead and/or average error for synthesis as a whole) associated with the retrieved patient independent synthesis matrix and sends the average error information to display 318 via message 317.

Thereafter, synthesization circuitry 322 utilizes the patient-independent synthesis matrix retrieved to synthesize the 12-lead EKG by applying the linear transform represented by the patient-independent synthesis matrix to the leads identified by EKG lead identification circuitry 308. And, in response to message 317, display 318 will display the accuracy factor/average error information in conjunction with each displayed synthesized lead and/or the synthesis as a whole, which will allow a user to make a confidence assessment as to the synthesized leads.

Shown in FIG. 3, is that the electrical signals from the various electrodes are simultaneously routed to synthesization circuitry 322 and EKG lead generation circuitry 325. EKG lead generation circuitry 325 generates the EKG leads that can be derived directly from the electrodes 302 physically connected to patient 300. As discussed, once the leads present have been identified and the appropriate synthesization matrix has been retrieved, synthesization occurs via the use of the leads identified and the synthesization matrix. The output of synthesization circuitry 322 will be the synthesized leads resulting from the application of the synthesization matrix to the leads identified by EKG identification circuitry.

Thereafter, signals 328 and 330 from synthesization circuitry 322 and EKG lead generation circuitry 325, respectively, are fed into synchronization circuitry 327, which receives the signals, temporally aligns them, and then outputs composite signal 332 to display 318. In response to composite signal 332, display 318 displays both the non-synthesized and synthesized leads, with indications of whether the lead is actual or synthesized.

Composite signal 332 is also output to signal processing and analysis circuitry 336. In response to composite signal 332, signal processing and analysis circuitry 336 processes and analyzes the information present and sends all or part of the results of that processing and analysis to storage 338 and display 318.

Composite signal 332 is also output to storage 338, which allows storage 338 to simultaneously store both the processed and analyzed data in addition to the composite signal 332 data upon which the synthesis and analysis was performed.

It has been mentioned that an illustrative embodiment of the present invention will allow checking of the synthesized leads for accuracy. How this can be done can be seen by reference to FIG. 3. Note that synthesization circuitry 322 is under control of EKG lead identification circuitry 308. Consequently, synthesization circuitry 322 only accepts and uses to synthesize the 12-lead EKG the leads which EKG lead identification circuitry deems to be active. As a consequence of this an EKG technician (not shown) can add one or more additional electrodes which can give rise to one or more actual EKG leads. Since the EKG synthesization circuitry 322 will ignore these leads until notified otherwise by EKG lead identification circuitry 308, the additional actual lead or leads will be run through EKG lead generation circuitry 325 and thereafter be displayed on display 318 virtually contemporaneously with the synthesized leads, thereby allowing an easy visual check as to the accuracy of the lead or leads that are being synthesized from the leads originally identified by EKG lead identification circuitry 308.

Additionally, shown is that composite signal 332 is also output to actual versus synthesized lead comparison circuitry 334. In response to composite signal 332, actual versus synthesized lead comparison circuitry 334 compares and analyzes the accuracy of any synthesized lead for which any actual, generated lead is also present (or, for any user-selectable subset of same), sends the results of that processing and analysis to display 318 via message 335.

A method and system have been set forth, above, which allow the synthesis of one or more leads of the 12-lead electrocardiograph from a subset of the electrodes normally utilized to provide the 12-lead electrocardiograph. A situation wherein such method and system would prove to be particularly useful would be where a patient's acuity makes impractical the use of the full electrode set necessary for construction of the 12-lead electrocardiograph, but where the 12-lead electrocardiograph is needed. Because the method and system utilize patient independent transformations and does not require the obtainment of a 12-lead electrocardiograph prior to providing the synthesis, such synthesis could still be done even though the 12-lead electrocardiograph itself could not be placed.

Another situation in which the method and system would prove useful would be where a patient's acuity makes impractical the use of the full electrode set necessary for construction of the 12-lead electrocardiograph, but where the 12-lead electrocardiograph is needed, and where such patient's acuity changes frequently making it necessary to frequently change the electrode set present. Because the method and system utilize patient independent transformations for many different sets and does not require the obtainment of a 12-lead electrocardiograph prior to providing the synthesis, such synthesis could still be done even though the electrode set was constantly changing and even though the 12-lead electrocardiograph itself could not be placed.

Yet another situation in which the method and system would prove useful would be where a monitoring physician decides that he wants to periodically check the accuracy of one or more of the leads synthesized. The method and system allows such checking to be done merely by the addition of one or more extra electrodes. Furthermore, if the physician finds that the synthesis is inadequate, the method and system will allow that the newly acquired lead be utilized and that a new synthesis based upon the newly acquired lead be generated. Because the method and system utilize patient independent transformations for many different subsets drawn from the set of leads utilized to construct the 12-lead electrocardiograph, and does not require the obtainment of a 12-lead electrocardiograph prior to providing the synthesis, such synthesis could still be done even though the electrode set was constantly changing and even though the 12-lead electrocardiograph itself could not be placed.

While the invention has been particularly shown and described with reference to a preferred embodiment, it will be understood by those skilled in the art that various changes in form and detail may be made therein without departing from the spirit and scope of the invention. For example, although the method and system have been, for the most part, described in relation to patient-independent synthesis matrices, it will be recognized by those within in the art that many of the features of the present invention may be practiced via the use of patient-dependent synthesis matrices. For example, for the most part, the method and system shown and described with respect to FIGS. 1, 2A, 2B, 2C and 3, could all be performed by gathering and storing a number of patient-dependent synthesis matrices and thereafter utilizing such stored patient-dependent synthesis matrices in the fashion described for patient-independent matrices. Of course, there are exceptions to the foregoing statement, (e.g., the patient-profile option will only work with patient-independent matrices), but much of the disclosure herein can be utilized with patient-dependent matrices, with only minor modifications.

What is claimed is:

1. A method for synthesizing a 12-lead electrocardiograph utilizing fewer than the 12 leads provided by a full electrode set, said method comprising the steps of:

attaching a subset of the full electrode set to a patient;

identifying a subset of 12-lead electrocardiograph leads formed by said attached subset of the full electrode set;

in response to said identified subset of 12-lead electrocardiograph leads, recalling a synthesis matrix;

in response to said recalled synthesis matrix, recalling an accuracy factor associated with said recalled synthesis matrix; and synthesizing one or more 12-lead electrocardiograph leads by applying said recalled synthesis matrix and said recalled accuracy factor associated with said recalled synthesis matrix to said identified subset of 12-lead electrocardiograph leads formed by said attached subset of the full electrode set.

2. The method of claim 1, wherein said step of recalling a synthesis matrix associated with said identified subset of 12-lead electrocardiograph leads formed by said attached subset further comprises the steps of:

designating a patient profile; and recalling a patient-independent synthesis matrix associated with both said designated patient profile and said identified subset of 12-lead electrocardiograph leads formed by said attached subset of the full electrode set.

3. The method of claim 1, wherein said step of recalling said accuracy factor associated with said recalled synthesis matrix further comprises the step of recalling an accuracy factor indicative of the accuracy of each individual synthesized lead to be generated by the utilization of said recalled synthesis matrix.

4. The method of claim 3, wherein said step of recalling said accuracy factor indicative of the accuracy of each individual synthesized lead to be generated by the utilization of said recalled synthesis matrix further comprises the step of recalling a standard deviation of said each representative individual synthesized lead from correspondent actual leads in a database utilized to generate said synthesis.

5. The method of claim 3, wherein said step of recalling said accuracy factor indicative of the accuracy of each individual synthesized lead to be generated by the utilization of said recalled synthesis matrix further comprises the step of recalling an average accuracy factor drawn upon a standard deviation of said each representative individual synthesized lead from correspondent actual leads in a database utilized to generate said synthesis matrix.

6. The method of claim 1, wherein said step of recalling a synthesis matrix further comprises the step of recalling a synthesis matrix associated with said identified subset of 12-lead electrocardiograph leads formed by said attached subset of the full electrode set.

7. The method of claim 6, wherein said step of recalling a synthesis matrix associated with said identified subset of 12-lead electrocardiograph leads formed by said attached subset of the full electrode set further comprises the steps of recalling a patient-independent synthesis matrix associated with said identified subset of 12-lead electrocardiograph leads formed by said attached subset of the full electrode set.

8. The method of claim 6, wherein said step of recalling a synthesis matrix associated with said identified subset of 12-lead electrocardiograph leads formed by said attached subset of the full electrode set further comprises the steps of recalling a patient-dependent synthesis matrix associated with said identified subset of 12-lead electrocardiograph leads formed by said attached subset of the full electrode set.

9. A method for quickly and efficiently producing multiple syntheses of 12-lead electrocardiographs utilizing fewer than the 12 leads provided by a full electrode set, said method comprising the steps of:
synthesizing one or more 12-lead electrocardiograph leads from a first subset of a patient's physically present 12-lead electrocardiograph leads; and
in response to user-defined parameters, synthesizing one or more 12-lead electrocardiograph leads from a second subset, different than said first subset, of a patient's physically present 12-lead electrocardiograph leads.

10. The method of claim 9, wherein said step of synthesizing one or more 12-lead electrocardiograph leads from a first subset of a patient's physically present 12-lead electrocardiograph leads further comprises the steps of:
attaching a first subset of the full electrode set to said patient;
identifying a first subset of 12-lead electrocardiograph leads formed by said attached first subset of the full electrode set; and
synthesizing one or more 12-lead electrocardiograph leads from said identified first subset of 12-lead electrocardiograph leads formed by said attached first subset of the full electrode set.

11. The method of claim 10, wherein said step of synthesizing from said identified first subset further comprises the steps of:
in response to said identified first subset of 12-lead electrocardiograph leads, recalling a first synthesis matrix; and
synthesizing one or more 12-lead electrocardiograph leads by applying said recalled first synthesis matrix to said identified first subset of 12-lead electrocardiograph leads formed by said attached first subset of the full electrode set.

12. The method of claim 11, wherein said step of recalling a first synthesis matrix further comprises the step of recalling a first patient-independent synthesis matrix associated with said identified first subset of 12-lead electrocardiograph leads formed by said attached first subset of the full electrode set.

13. The method of claim 11, wherein said step of recalling a first synthesis matrix further comprises the step of recalling a first patient-dependent synthesis matrix associated with said identified first subset of 12-lead electrocardiograph leads formed by said attached first subset of the full electrode set.

14. The method of claim 10, wherein said step of synthesizing from said identified first subset further comprises the steps of:
designating a patient profile;
recalling a first patient-independent synthesis matrix associated with both said designated patient profile and said identified first subset of 12-lead electrocardiograph leads formed by said attached first subset of the full electrode set; and
synthesizing one or more 12-lead electrocardiograph leads by applying said recalled first patient-independent synthesis matrix associated with both said designated patient profile and said identified first subset of 12-lead electrocardiograph leads formed by said attached first subset of the full electrode set to said identified first subset of 12-lead electrocardiograph leads formed by said attached first subset of the full electrode set.

15. The method of claim 9, wherein said step of synthesizing one or more 12-lead electrocardiograph leads from a second subset of a patient's physically present 12-lead electrocardiograph leads further comprises the steps of:
attaching a second subset, different from said attached first subset, of the full electrode set to said patient;
identifying a second subset of 12-lead electrocardiograph leads formed by said attached second subset of the full electrode set; and
synthesizing one or more 12-lead electrocardiograph leads from said identified second subset of 12-lead electrocardiograph leads formed by said attached second subset of the full electrode set.

16. The method of claim 15, wherein said step of synthesizing from said identified second subset further comprises the steps of:
in response to said identified second subset of 12-lead electrocardiograph leads, recalling a second synthesis matrix; and
synthesizing one or more 12-lead electrocardiograph leads by applying said recalled second synthesis matrix to said identified second subset of 12-lead electrocardiograph leads formed by said attached second subset of the full electrode set.

17. The method of claim 16, wherein said step of recalling a second synthesis matrix further comprises the step of recalling a second patient-independent synthesis matrix associated with said identified second subset of 12-lead electrocardiograph leads formed by said attached second subset of the full electrode set.

18. The method of claim 16, wherein said step of recalling a second synthesis matrix further comprises the step of recalling a second patient-dependent synthesis matrix associated with said identified second subset of 12-lead electrocardiograph leads formed by said attached second subset of the full electrode set.

19. The method of claim 15, wherein said step of synthesizing from said identified second subset further comprises the steps of:
designating a patient profile;
recalling a second patient-independent synthesis matrix associated with both said designated patient profile and said identified second subset of 12-lead electrocardiograph leads formed by said attached first subset of the full electrode set; and
synthesizing one or more 12-lead electrocardiograph leads by applying said recalled second patient-independent synthesis matrix associated with both said designated patient profile and said identified second subset of 12-lead electrocardiograph leads formed by said attached first subset of the full electrode set to said identified second subset of 12-lead electrocardiograph leads formed by said attached first subset of the full electrode set.

20. The method of claim 9, wherein said step of synthesizing one or more 12-lead electrocardiograph leads from a first subset of a patient's physically present 12-lead electrocardiograph leads further comprises the step of synthesizing one or more 12-lead electrocardiograph leads by applying a recalled synthesis matrix and a recalled accuracy factor associated with said recalled synthesis matrix to an identified subset of 12-lead electrocardiograph leads formed by an attached subset of the full electrode set.

21. The method of claim 9, wherein said step of synthesizing one or more 12-lead electrocardiograph leads from a second subset of a patient's physically present 12-lead electrocardiograph leads further comprises the step of synthesizing one or more 12-lead electrocardiograph leads by applying a recalled synthesis matrix and a recalled accuracy factor associated with said recalled synthesis matrix to an identified subset of 12-lead electrocardiograph leads formed by an attached subset of the full electrode set.

22. A method for assessing the accuracy of synthesized electrocardiograph leads, said method comprising:

synthesizing one or more electrocardiograph leads;

attaching one or more additional electrodes to the patient;

generating one or more electrocardiograph leads from said attached one or more additional electrodes; and comparing said generated one or more electrocardiograph leads with correspondent synthesized one or more electrocardiograph leads wherein said step of synthesizing one or more 12-lead electrocardiograph leads further comprises the step of synthesizing one or more 12-lead electrocardiograph leads by applying a recalled synthesis matrix and a recalled accuracy factor associated with said recalled synthesis matrix to an identified subset of 12-lead electrocardiograph leads formed by an attached subset of the full electrode set.

23. The method of claim 22, wherein said step of synthesizing one or more 12-lead electrocardiograph leads further comprises the steps of:

synthesizing one or more 12-lead electrocardiograph leads from a first subset of a patient's physically present 12-lead electrocardiograph leads; and in response to user-defined parameters, synthesizing one or more 12-lead electrocardiograph leads from a second subset, different than said first subset, of a patient's physically present 12-lead electrocardiograph leads.

24. The method of claim 22, wherein said step of comparing further comprises the step of simultaneously displaying said generated one or more electrocardiograph leads with correspondent synthesized one or more electrocardiograph leads.

25. The method of claim 22, wherein said step of comparing further comprises the step of automatically comparing said generated one or more electrocardiograph leads with correspondent synthesized one or more electrocardiograph leads.

26. A system for synthesizing a 12-lead electrocardiograph utilizing fewer than the 12 leads provided by a full electrode set, said system comprising:

means for attaching a subset of the full electrode set to a patient;

means for identifying a subset of 12-lead electrocardiograph leads formed by said attached subset of the full electrode set;

means, responsive to said identified subset of 12-lead electrocardiograph leads, for recalling a synthesis matrix;

means, responsive to said recalled synthesis matrix, for recalling an accuracy factor associated with said recalled synthesis matrix; and means for synthesizing one or more 12-lead electrocardiograph leads by applying said recalled synthesis matrix and said recalled accuracy factor associated with said recalled synthesis matrix to said identified subset of 12-lead electrocardiograph leads formed by said attached subset of the full electrode set.

27. The system of claim 26, wherein said means for recalling a synthesis matrix associated with said identified subset of 12-lead electrocardiograph leads formed by said attached subset further comprises:

means for designating a patient profile; and means for recalling a patient-independent synthesis matrix associated with both said designated patient profile and said identified subset of 12-lead electrocardiograph leads formed by said attached subset of the full electrode set.

28. The system of claim 26, wherein said means for recalling said accuracy factor associated with said recalled synthesis matrix further comprises means for recalling an accuracy factor indicative of the accuracy of each individual synthesized lead to be generated by the utilization of said recalled synthesis matrix.

29. The system of claim 28, wherein said means for recalling said accuracy factor indicative of the accuracy of each individual synthesized lead to be generated by the utilization of said recalled synthesis matrix further comprises means for recalling a standard deviation of said each representative individual synthesized lead from correspondent actual leads in a database utilized to generate said synthesis.

30. The system of claim 28, wherein said means for recalling said accuracy factor indicative of the accuracy of each individual synthesized lead to be generated by the utilization of said recalled synthesis matrix further comprises means for recalling an average accuracy factor drawn upon a standard deviation of said each representative individual synthesized lead from correspondent actual leads in a database utilized to generate said synthesis matrix.

31. The system of claim 26, wherein said means for recalling a synthesis matrix further comprises means for recalling a synthesis matrix associated with said identified subset of 12-lead electrocardiograph leads formed by said attached subset of the full electrode set.

32. The system of claim 31, wherein said means for recalling a synthesis matrix associated with said identified subset of 12-lead electrocardiograph leads formed by said attached subset of the full electrode set further comprises means for recalling a patient-independent synthesis matrix associated with said identified subset of 12-lead electrocardiograph leads formed by said attached subset of the full electrode set.

33. The system of claim 31, wherein said means for recalling a synthesis matrix associated with said identified subset of 12-lead electrocardiograph leads formed by said attached subset of the full electrode set further comprises means for recalling a patient-dependent synthesis matrix associated with said identified subset of 12-lead electrocardiograph leads formed by said attached subset of the full electrode set.

34. A system for quickly and efficiently producing multiple syntheses of 12-lead electrocardiographs utilizing fewer than the 12 leads provided by a full electrode set, said system comprising:

means for synthesizing one or more 12-lead electrocardiograph leads from a first subset of a patient's physically present 12-lead electrocardiograph leads; and means, responsive to user-defined parameters, for synthesizing one or more 12-lead electrocardiograph leads from a second subset, different than said first subset, of a patient's physically present 12-lead electrocardiograph leads.

35. The system of claim 34, wherein said means for synthesizing one or more 12-lead electrocardiograph leads from a first subset of a patient's physically present 12-lead electrocardiograph leads further comprises:

means for attaching a first subset of the full electrode set to said patient;

means for identifying a first subset of 12-lead electrocardiograph leads formed by said attached first subset of the full electrode set; and means for synthesizing one or more 12-lead electrocardiograph leads from said identified first subset of 12-lead electrocardiograph leads formed by said attached first subset of the full electrode set.

36. The system of claim 35, wherein said means for synthesizing from said identified first subset further comprises:

means, responsive to said identified first subset of 12-lead electrocardiograph leads, for recalling a first synthesis matrix; and means for synthesizing one or more 12-lead electrocardiograph leads by applying said recalled first synthesis matrix to said identified first subset of 12-lead electrocardiograph leads formed by said attached first subset of the full electrode set.

37. The system of claim 36, wherein said means for recalling a first synthesis matrix further comprises means for recalling a first patient-independent synthesis matrix associated with said identified first subset of 12-lead electrocardiograph leads formed by said attached first subset of the full electrode set.

38. The system of claim 36, wherein said means for recalling a first synthesis matrix further comprises means for recalling a first patient-dependent synthesis matrix associated with said identified first subset of 12-lead electrocardiograph leads formed by said attached first subset of the full electrode set.

39. The system of claim 35, wherein said means for synthesizing from said identified first subset further comprises:

means for designating a patient profile;

means for recalling a first patient-independent synthesis matrix associated with both said designated patient profile and said identified first subset of 12-lead electrocardiograph leads formed by said attached first subset of the full electrode set; and means for synthesizing one or more 12-lead electrocardiograph leads by applying said recalled first patient-independent synthesis matrix associated with both said designated patient profile and said identified first subset of 12-lead electrocardiograph leads formed by said attached first subset of the full electrode set to said identified first subset of 12-lead electrocardiograph leads formed by said attached first subset of the full electrode set.

40. The system of claim 34, wherein said means for synthesizing one or more 12-lead electrocardiograph leads from a second subset of a patient's physically present 12-lead electrocardiograph leads further comprises:

means for attaching a second subset, different from said attached first subset, of the full electrode set to said patient;

means for identifying a second subset of 12-lead electrocardiograph leads formed by said attached second subset of the full electrode set; and means for synthesizing one or more 12-lead electrocardiograph leads from said identified second subset of 12-lead electrocardiograph leads formed by said attached second subset of the full electrode set.

41. The system of claim 40, wherein said means for synthesizing from said identified second subset further comprises:

means, responsive to said identified second subset of 12-lead electrocardiograph leads, for recalling a second synthesis matrix; and means for synthesizing one or more 12-lead electrocardiograph leads by applying said recalled second synthesis matrix to said identified second subset of 12-lead electrocardiograph leads formed by said attached second subset of the full electrode set.

42. The system of claim 40, wherein said means for synthesizing from said identified second subset further comprises:

means for designating a patient profile;

means for recalling a second patient-independent synthesis matrix associated with both said designated patient profile and said identified second subset of 12-lead electrocardiograph leads formed by said attached first subset of the full electrode set; and means for synthesizing one or more 12-lead electrocardiograph leads by applying said recalled second patient-independent synthesis matrix associated with both said designated patient profile and said identified second subset of 12-lead electrocardiograph leads formed by said attached first subset of the full electrode set to said identified second subset of 12-lead electrocardiograph leads formed by said attached first subset of the full electrode set.

43. The system of claim 41, wherein said means for recalling a second synthesis matrix further comprises means for recalling a second patient-independent synthesis matrix associated with said identified second subset of 12-lead electrocardiograph leads formed by said attached second subset of the full electrode set.

44. The system of claim 41, wherein said means for recalling a second synthesis matrix further comprises means for recalling a second patient-dependent synthesis matrix associated with said identified second subset of 12-lead electrocardiograph leads formed by said attached second subset of the full electrode set.

45. The system of claim 34, wherein said means for synthesizing one or more 12-lead electrocardiograph leads from a first subset of a patient's physically present 12-lead electrocardiograph leads further comprises means for synthesizing one or more 12-lead electrocardiograph leads by applying a recalled synthesis matrix and a recalled accuracy factor associated with said recalled synthesis matrix to an identified subset of 12-lead electrocardiograph leads formed by an attached subset of the full electrode set.

46. The system of claim 34, wherein said means for synthesizing one or more 12-lead electrocardiograph leads from a second subset of a patient's physically present 12-lead electrocardiograph leads further comprises means for synthesizing one or more 12-lead electrocardiograph leads by applying a recalled synthesis matrix and a recalled accuracy factor associated with said recalled synthesis matrix to an identified subset of 12-lead electrocardiograph leads formed by an attached subset of the full electrode set.

47. A system for assessing the accuracy of synthesized electrocardiograph leads, said system comprising:
   means for synthesizing one or more electrocardiograph leads;
   means for attaching one or more additional electrodes to the patient;
   means for generating one or more electrocardiograph leads from said attached one or more additional electrodes; and
   means for comparing said generated one or more electrocardiograph leads with correspondent synthesized one or more electrocardiograph leads wherein said means for synthesizing one or more 12-lead electrocardiograph leads further comprises means for synthesizing one or more 12-lead electrocardiograph leads by applying a recalled synthesis matrix and a recalled accuracy factor associated with said recalled synthesis matrix to an identified subset of 12-lead electrocardiograph leads formed by an attached subset of the full electrode set.

48. The system of claim 47, wherein said means for synthesizing one or more 12-lead electrocardiograph leads further comprises:
   means for synthesizing one or more 12-lead electrocardiograph leads from a first subset of a patient's physically present 12-lead electrocardiograph leads; and
   means, responsive to user-defined parameters, for synthesizing one or more 12-lead electrocardiograph leads from a second subset, different than said first subset, of a patient's physically present 12-lead electrocardiograph leads.

49. The system of claim 47, wherein said means for comparing further comprises means for simultaneously displaying said generated one or more electrocardiograph leads with correspondent synthesized one or more electrocardiograph leads.

50. The system of claim 47, wherein said means for comparing further comprises means for automatically comparing said generated one or more electrocardiograph leads with correspondent synthesized one or more electrocardiograph leads.

* * * * *